Figure 1:
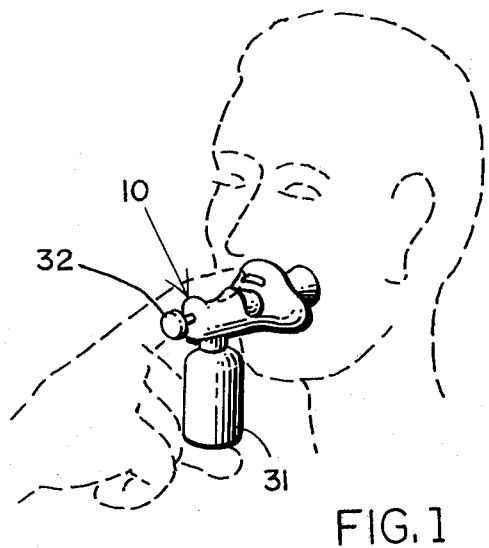
Figure 2:
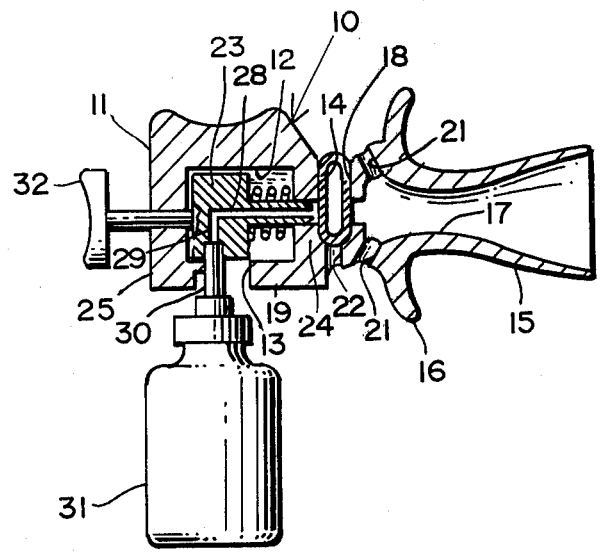

United States Patent [19]

Harris

[11] 3,998,226

[45] Dec. 21, 1976

[54] INHALATION DEVICE FOR ENCAPSULATED CONCENTRATES

[75] Inventor: Arthur M. Harris, Miami Shores, Fla.

[73] Assignee: Edward G. Gomez, Coral Gables, Fla.

[22] Filed: Sept. 22, 1975

[21] Appl. No.: 615,420

[52] U.S. Cl. .............................. 128/266; 128/203; 128/209; 128/201
[51] Int. Cl.² ................ A61M 15/02; A61M 13/00
[58] Field of Search .......... 128/203, 201, 198, 206, 128/207, 208, 187, 209, 210, 266, 265; 239/142, 143; 222/193, 82, 83

[56] References Cited

UNITED STATES PATENTS

| 2,307,986 | 1/1943 | Bolte et al. | 128/266 |
| 3,653,380 | 4/1972 | Hansen | 128/203 |
| 3,809,084 | 5/1974 | Hansen | 128/266 |
| 3,809,294 | 5/1974 | Torgeson | 128/203 |
| 3,888,253 | 6/1975 | Watt et al. | 128/208 |

FOREIGN PATENTS OR APPLICATIONS 1,338,254  11/1973  United Kingdom ............... 128/266

Primary Examiner—Robert W. Michell
Assistant Examiner—Henry J. Recla
Attorney, Agent, or Firm—Salvatore G. Militana

[57] ABSTRACT

An inhalation device for encapsulated concentrates having a capsule piercing hypodermic needle, a mouthpiece and a cavity for receiving a capsule containing a granular medicant and the like, whereby the device is actuated to pierce the capsule to form a pair of aligned openings. An aerosol bottle is so mounted on the device that fluid under pressure is conducted through the hypodermic needle and through the aligned openings in the capsule to disperse particles of the medicant thereby. The mixture of fluid under pressure and particles of medicant are then discharged through a venturi passageway in the mouthpiece and into a person's mouth.

3 Claims, 5 Drawing Figures

U.S. Patent  Dec. 21, 1976  3,998,226

INHALATION DEVICE FOR ENCAPSULATED CONCENTRATES

BACKGROUND OF THE INVENTION

1. Field Of The Invention

This invention relates to dispensing devices of granular material and is especially directed to an inhalation device for encapsulated concentrates.

2. Description Of The Prior Art

At the present time there are two types of inhalation devices for introducing a granular concentrate such as a medication into one's mouth. The older type of these two devices requires a person to place a desired dosage of the material in a chamber into which gas under pressure is permitted to blow the material into one's mouth. The other type of device provides for piercing a capsule containing the granular medication and then passing a stream of air therealong to pick up the granules of material that fall out of the capsule into the stream of gas under pressure and discharge same in the user's mouth. In the first category of dispensers, the amount of granular material brought into the stream of gas under pressure and dispensed thereby is determined by the area of the granular mass exposed to the stream of gas under pressure. It is readily noted that the amount of granular material will be greatest at the start of the inhalation procedure and diminishes as the amount of material in the dispenser decreases. With the use of medicaments, chemicals and the like, the high concentration at the start of the inhalation process may be harmful.

In the instance of the devices that pierce a capsule, the amount of granular material being picked up by a stream of high pressure gas is determined by the rate at which the granular material is able to flow through the opening made into the capsule. As can be readily noted, the concentration of granular material will not be constant but will vary with the same device under like conditions due to such factors as size of opening made in the capsule and the aspiration or suction effect of the gas as it flow past the capsule. For example, more granules of medication will be brought into the stream of flowing gas if the device is vibrated to cause the granules to move toward the opening in the capsule as against the device being held motionless and the granules remaining motionless in the capsule until they come under the influence of the suction created by the flowing gas. The present invention contemplates avoiding the above indicated objections to the conventional inhalator devices for granular medication.

BRIEF SUMMARY OF THE INVENTION

Therefore a principal object of the present invention is to provide an inhalation device for encapsulated concentrates with a device which discharges a constant concentration of granular particles in a stream of gas under pressure.

Another object of the present invention is to provide an inhalation device for encapsulated concentrates which is compact in construction, shaped to fit comfortably in one's hand and constructed so that it can be held and operated with the fingers of one hand to puncture the capsule and discharge the concentrate through a mouth piece positioned in the user's mouth.

A further object of the present invention is to provide an inhalation device for encapsulated concentrates that is simple in construction, inexpensive in cost, most effective in dispensing granular material such as medicaments into one's mouth as well as requiring little preparatory effort when one is ready to use the device.

A still further object of the present invention is to provide an inhalation device for encapsulated concentrates with a cavity so shaped and sized to receive a capsule which when pierced by a hypodermic needle will permit gas under pressure to flow only through holes formed in the sides of the capsule by a hypodermic needle.

With these and other objects in view, the invention will be best understood from a consideration of the following detailed description taken in connection with the accompanying drawing forming a part of this specification, with the understanding, however, that the invention is not confined to any strict conformity with the showing of the drawing but may be changed or modified so long as such changes or modifications mark no material departure from the salient features of the invention as expressed in the appended claims.

BRIEF DESCRIPTION OF THE SEVERAL VIEWS OF THE DRAWING

In the drawing:

FIG. 1 is a perspective view of my inhalator device for encapsulated concentrates showing the user in dotted lines.

FIG. 2 is a longitudinal cross sectional view with a capsule in place in the device.

FIG. 3 is a similar view showing the manner of piercing the capsule.

FIG. 4 is a similar view showing the manner of dispensing the concentrate into the user's mouth which is shown in dotted lines.

FIG. 5 is a similar view of an alternate structure of my inhalation device.

DETAILED DESCRIPTION OF THE PREFERRED EMBODIMENTS

Referring to the drawing wherein like numerals are used to refer to similar parts throughout the several views, the numeral 10 refers to an inhalator device for encapsulated concentrates constructed in accordance with my invention and consisting of a body member 11 having a centrally disposed chamber 12. The chamber 12 is provided with a pair of openings 13 and 14 at the bottom wall 19 and front wall 24, respectively of the body member 11. Extending integrally with the body member 10 at its forward end portion is a cone shaped mouthpiece 15 about which extends a radially extending flange portion 16. Communicating with the opening 14 is a Venturitype passageway 17 extending the full length of the mouthpiece 15. Between the body member 11 and the mouthpiece 15 is a cavity 18 for receiving a capsule 20 containing concentrates such as medication, chemical, etc. in granular form. The cavity 18 is of such size and shape to receive the capsule 20 and contain it therein in a snug manner so as to prevent any leakage of gas under pressure except as indicated hereinafter. Adjacent the cavity 18 there is a plurality of bores 21 extending about the base of the flange 16 and permitting air to be aspirated into the Venturi passage 17 when the device 10 is being actuated as explained hereinafter. At the base of the cavity 18 there is a further bore 22 whose main functions are to provide an access to allow for the ejection of a used capsule and to prevent any collection of granules of concentrate that may spill out of the capsule 20 during the normal operation of the inhalator 10. If there were no opening 22 in the body member 11, the granules of matter would accumulate in the cavity 18 and prevent the proper positioning of the capsules 20 in the cavity 18.

Within the chamber 12 is a slide block 23 mounted for lateral movement therein with a coil spring 26 mounted between the forward edge portion of the slide block 23 and the front wall 24 of the chamber 12 to yieldingly urge the slide block 23 to engage the rear wall 25 of the chamber 12. Mounted on the front wall portion of the slide block 23 is a hypodermic needle 27 in communication with a fluid passageway 28 that extends to the center of the slide block 23. A further fluid passageway 29 extends upwardly in the center of the slide block permitting the flow of fluid under pressure from an inlet pipe 30 to the fluid passageway 28. The inlet pipe 30 is connected to a conventional aerosol bottle 31. The inlet pipe extends through the opening 13 of the body member 11. To effect the sliding movement of the slide block 23 there is provided a plunger consisting of a push handle 32 mounted on the end of a stem 33 that extends through an opening 34 in the body member 11.

Figure 3:
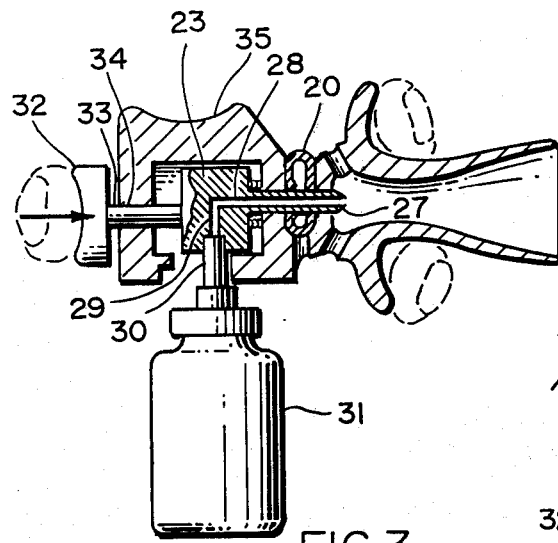
Figure 4:
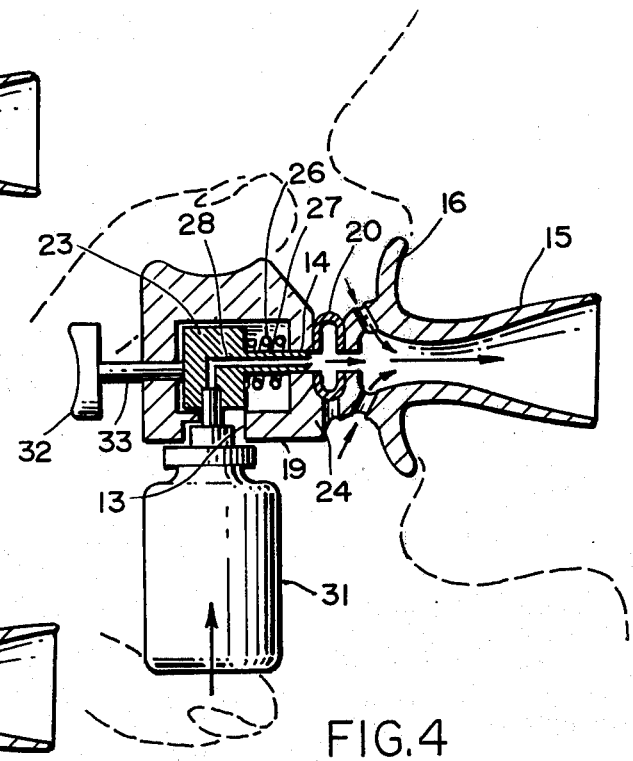
Figure 5:
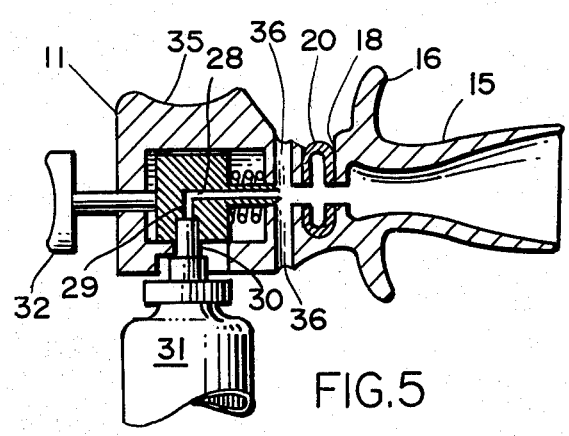

In the normal use of my inhalator 10, a capsule 20 is inserted into the cavity 18 and pushed downwardly therein until bottomed. The user then places his index finger and middle finger about the flange 16 and with his thumb he pushes against the knob or handle 32 against the spring pressure 26. The slide block 23 then slides forwardly causing the hypodermic needle 27 to pierce through the capsule 20 as shown by FIG. 3. Pressure against the knob 32 is released and the spring 26 causes the slide block 23 to return to its original position. The needle 27 forms a pair of aligned openings in the wall of the capsule 20. Now the index finger is placed on the top contoured portion 35 of the body member 11, the thumb on the bottom of the aerosol bottle 31 and the mouthpiece 15 is placed into the mouth of the user as shown in dotted lines by FIG. 4. The user then inhales deeply as the index finger and thumb are squeezed together to cause the opening of the valve (not shown) in the conventional aerosol bottle 31. Fluid under pressure will now flow out of the bottle 31 through the fluid passageways 29, 28, through the hypodermic needle 27 and through the aligned openings formed in the capsule 20. The fluid under pressure passing through the capsule 20 carries along with it particles or granules of medication, etc. contained in the capsule 20. When this mixture of fluid under pressure and particles of medication enters the Venturi passageway 17, air is aspirated through the openings 21 to dilute the mixture of fluid and particles with the resultant mixture being discharged into the user's mouth. So long as there are granules of material in the capsule 20 in the space between the two holes formed by the hypodermic needle 27, the concentration of granules being discharged through the Venturi 17 will be constant since all of the gas being discharged by the aerosol bottle 31 has to pass through these holes in the capsule 20.

Instead of having openings 21 in the mouthpiece 15, openings 36 can be formed in the body member 11 adjacent the cavity 18 so that the mixture of aspirated air and fluid under pressure occurs prior to passing through the capsule 20 to dispersing particles of concentrate into the user's mouth. The aerosol bottle 31 can be readily replaced when the fluid under pressure therein has been exhausted by merely pulling the bottle 31 from the inlet pipe 30 and replacing it with a new bottle of aerosol.

Having disclosed my invention, what I claim as new and desire to secure by Letters Patent is:

1. An inhalation device for encapsulated concentrates comprising a body member having a chamber having a front and rear wall, a block member slidably mounted in said chamber from a first position to a second position, spring means yieldingly urging said block member to said first position rearwardly in said chamber, a mouthpiece mounted on the front wall of said body member, said mouthpiece having a passageway extending longitudinally thereof, a duct in said front wall extending from said chamber to said passageway, an open cavity for receiving a capsule formed in said mouthpiece adjacent to said front wall and in substantial alignment with said duct, a hyperdermic needle mounted forwardly of said slide block in axial alignment with said duct and extending beyond said cavity when said block is in said second position, means for sliding said block member to said second position forwardly in said chamber whereby said needle slides substantially beyond said cavity and is adapted to form aligned openings in a capsule positioned in said cavity, and an inlet duct for receiving an aerosol bottle communicating with said hyperdermic needle whereby fluid under pressure from said aerosol bottle passes through said ducts and said aligned openings to disperse the granules contained in said capsule into said passageway and be discharged through said mouthpiece.

2. The structure as recited by claim 1 wherein openings are formed adjacent said cavity for aspirating air into said passageway.

3. The structure as recited by claim 2 wherein said means for sliding said block member comprises a stem extending from said block member through an opening in a rear wall of said block member and a finger engaging member mounted on the free end of said stem.

* * * * *